United States Patent
Schaaf et al.

(10) Patent No.: US 6,242,613 B1
(45) Date of Patent: Jun. 5, 2001

(54) STABLE ARYLPYRROLE PARTICLES, PROCESS FOR THEIR PREPARATION AND SUSPENSION CONCENTRATE COMPOSITIONS COMPRISING THEM

(75) Inventors: Mimi Yih-Pei Chou Schaaf, Princeton, NJ (US); Steven Brunt, Yardley, PA (US); Jian James Xu, Princeton, NJ (US); Andrew Evelyn Goldsmith, Waterlooville; Anthony Francis Walker, Fareham, both of (GB); Patrick C. Mowery, Morrisville, PA (US); Edward S. Donoghue, Titusville, NJ (US); Srinivasan Rajan, Newton, PA (US)

(73) Assignee: American Cyanamid Co., Madison, NJ (US)

( * ) Notice: Subject to any disclaimer, the term of this patent is extended or adjusted under 35 U.S.C. 154(b) by 0 days.

(21) Appl. No.: 09/286,967

(22) Filed: Apr. 6, 1999

Related U.S. Application Data

(63) Continuation-in-part of application No. 08/903,201, filed on Jul. 15, 1997, now abandoned.
(60) Provisional application No. 60/023,045, filed on Aug. 2, 1996.

(51) Int. Cl.[7] .................... C07D 207/30; C07D 207/34
(52) U.S. Cl. .................. 548/560; 548/557; 548/561; 548/562; 548/563
(58) Field of Search ................... 548/560–563; 514/408, 424, 426, 427, 428

(56) References Cited

U.S. PATENT DOCUMENTS

| | | | |
|---|---|---|---|
| 5,010,098 | 4/1991 | Brown et al. | 514/426 |
| 5,233,051 | 8/1993 | Uhr et al. | 548/526 |
| 5,496,845 | 3/1996 | Martin et al. | 514/427 |

FOREIGN PATENT DOCUMENTS

| | | | |
|---|---|---|---|
| 2076937 | 1/1993 | (CA) | C07D/207/34 |
| 0 249 075 | 5/1987 | (EP) . | |
| 0 249 770 | 5/1987 | (EP) . | |
| 0 683 979 | 5/1995 | (EP) . | |

OTHER PUBLICATIONS

J.T. Pearson and G. Varney, "Crystal Growth Studies Involving Phase Transitions in Aqueous Drug Suspensions", Journal of Pharmacy and Pharmacology, vol. 21 (Suppl.) 1969, London GB pp. 60S–69S.

*Primary Examiner*—Jane C. Oswecki
(74) *Attorney, Agent, or Firm*—Barbara L. Renda; Barbara W. Maurer

(57) ABSTRACT

The present invention relates to arylpyrrole particles which are prepared by a process in which the particles are aged and milled, and pesticidal suspension concentrate compositions comprising them. The size of the particles of this invention remains surprisingly stable during storage.

5 Claims, 2 Drawing Sheets

STABLE ARYLPYRROLE PARTICLES, PROCESS FOR THEIR PREPARATION AND SUSPENSION CONCENTRATE COMPOSITIONS COMPRISING THEM

This is a continuation-in-part of application(s) Ser. No. 08/903,201 filed on Jul. 15, 1997, abandoned, the entire disclosure of which is hereby incorporated by reference, and claims the benefit of provisional Application No. 60/023,045 filed Aug. 2, 1996.

BACKGROUND OF THE INVENTION

Pests such as insects and acarids cause tremendous global economic losses by reducing crop yields and lowering crop quality. Arylpyrrole compounds are useful for the control of insect and acarid pests. However, it has been found that arylpyrrole particles present in suspension concentrate may not maintain a stable particle size. In particular, it has been found that certain arylpyrrole particles grow to an unacceptable size during storage.

Certain pesticidal arylpyrrole compounds and methods for their preparation and use are described in U.S. Pat. Nos. 5,010,098 and 5,233,051; and Canadian Patent Application Number 2,076,937. Chlorfenapyr (4-bromo-2-(p-chlorophenyl)-1-(ethoxymethyl)-5-(trifluoromethyl) pyrrole-3-carbonitrile) was the first arylpyrrole pesticide to be commercialized. Chlorfenapyr and methods for its preparation and use are described in U.S. Pat. No. 5,010,098.

Suspension concentrate compositions comprising arylpyrrole particles are disclosed in U.S. Pat. No. 5,496,845. However, it has been found that the particle size stability of the arylpyrrole compounds in the reference compositions is variable. Commonly, arylpyrrole particles known in the art increase in size during storage, i.e., an initial number of relatively small particles becomes a smaller number of larger particles. It is desirable to have particles whose sizes are predictably stable over time, to avoid undesired variations in the characteristics of formulations containing these particles.

SUMMARY OF THE INVENTION

The present invention provides stable arylpyrrole particles wherein more than about 20% of the arylpyrrole is in a stable crystalline form thereof.

The present invention further provides a process for the preparation of stable arylpyrrole particles which process comprises:
  a) providing a first mixture comprising arylpyrrole particles, a dispersing agent and water;
  b) keeping the first mixture in a temperature range of about 25° C. to 80° C. to obtain an aged mixture; and
  c) milling, if necessary, the aged mixture to obtain stabilized arylpyrrole particles.

The present invention also provides stable arylpyrrole particles prepared by the process of this invention, and suspension concentrate compositions comprising arylpyrrole particles of this invention.

It is, therefore, an object of the present invention to provide a process for stabilizing arylpyrrole particles.

It is another object of this invention to provide stable arylpyrrole particles.

It is a further object of this invention to provide suspension concentrate compositions which comprise stable arylpyrrole particles.

These and other objects and advantages of the present invention will become more apparent from the detailed description thereof set forth below, and from the appended claims.

DETAILED DESCRIPTION OF THE PREFERRED EMBODIMENTS

Figure 1:
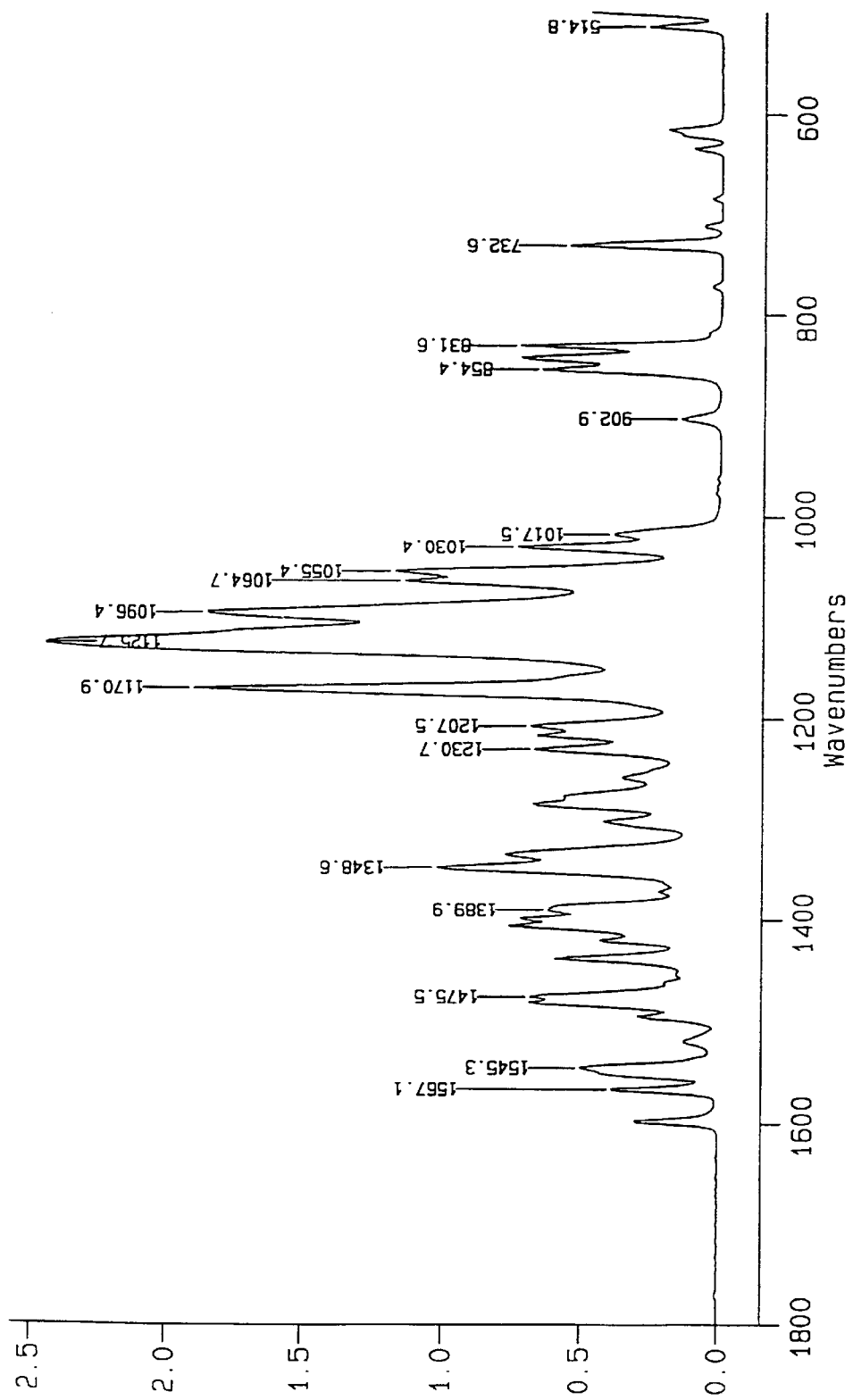
FIG. 1 is the characteristic infrared absorption spectrum of the chlorfenapyr polymorph designated as "Polymorph I".
Figure 2:
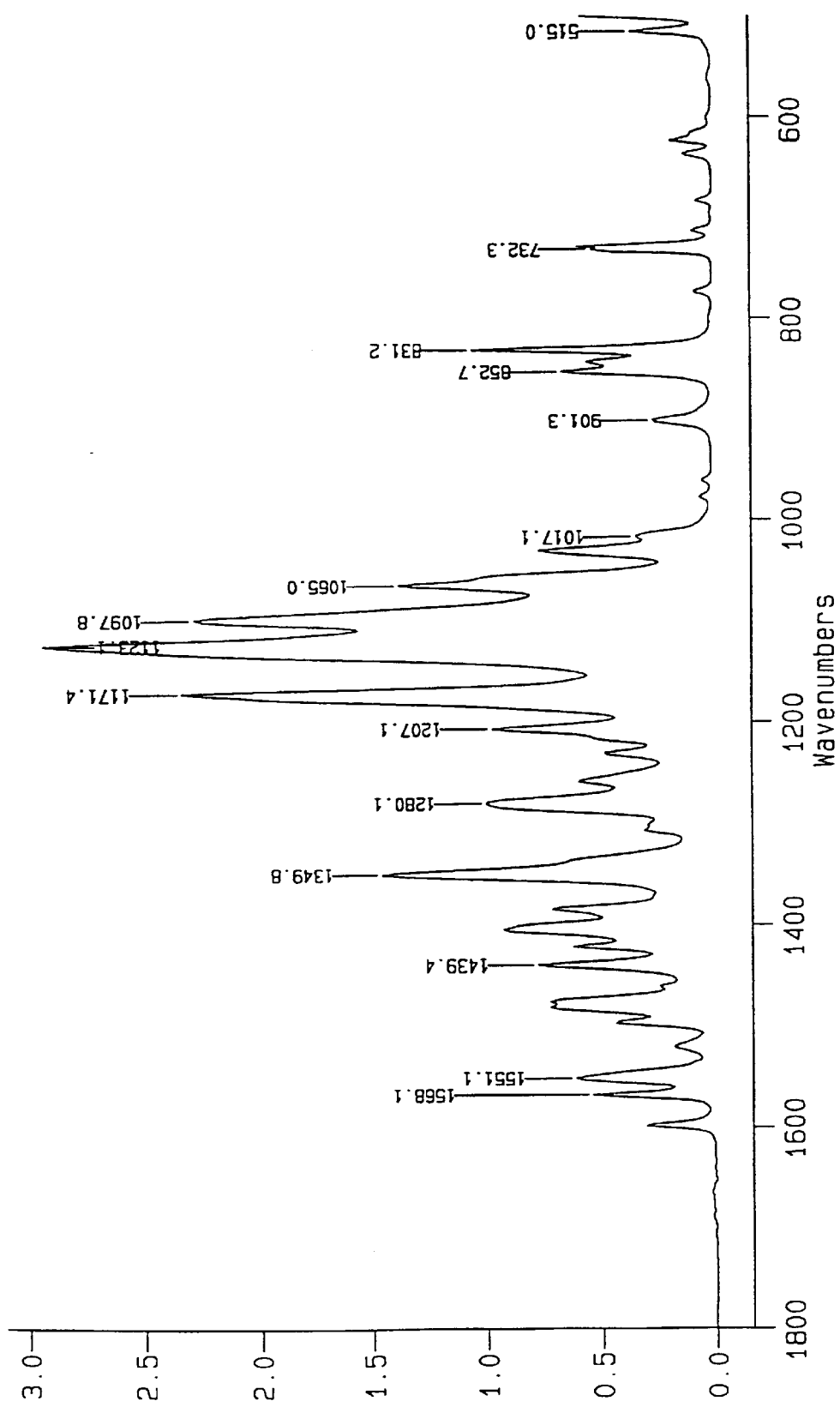
FIG. 2 is the characteristic infrared absorption spectrum of the chlorfenapyr polymorph designated as "Polymorph II".

In one important aspect, the present invention provides stable arylpyrrole particles which grow within allowable or acceptable limits during storage in suspension concentrate compositions. We have discovered that arylpyrroles may exist in at least two crystal forms. The predominant crystal forms of chlorfenapyr, for example, are designated herein as Polymorph I and Polymorph II. Polymorph I has a melting point of 95° C. and the characteristic infrared absorption spectrum shown in FIG. 1. Polymorph II has a melting point of 101° C. and the characteristic infrared absorption spectrum shown in FIG. 2.

We have further discovered that certain arylpyrrole crystal forms are more stable than other arylpyrrole crystal forms. Surprisingly, compositions containing chlorfenapyr particles having a Polymorph I to Polymorph II ratio greater than about 1:4 are significantly more storage stable than compositions having a Polymorph I to Polymorph II ratio of 1:4 to 0:1.

Advantageously, the present invention relates to arylpyrrole particles comprising a stabilizing amount of a stable crystal form of the arylpyrrole. The stabilizing amount of the stable crystal form is that amount which prevents unacceptable particle growth during storage in compositions comprising the arylpyrrole particles and water. Unacceptable particle growth may reduce the pesticidal efficacy of the arylpyrroles and/or detrimentally affects the physical properties of the compositions including their dilution/use characteristics.

Heretofore, the stability of arylpyrrole particles was unpredictable because commercial production methods provided particles having widely varying amounts of the stable crystal form. The existence and importance of the different crystal forms were not known and understood, and there was no known method for achieving predictably stable particles.

It has now been discovered that different crystal forms, or polymorphs, can be identified. It has also been found that arylpyrrole suspension concentrate compositions comprising a high percentage of one polymorph are more stable than suspension concentrate compositions comprising a low percentage of that polymorph. In particular, chlorfenapyr suspension concentrate compositions comprising chlorfenapyr particles containing a high percentage of Polymorph I are more stable than suspension concentrate compositions containing a low percentage of Polymorph I. Because the amount of each crystal form can be measured, stable arylpyrrole suspension concentrates can now be achieved consistently and predictably by forming the suspension from arylpyrrole particles having sufficient stable crystal content.

Arylpyrrole particles having the desired amount of stable crystal form may be selected from among the variety of particles formed by commercial production processes. Batches of an arylpyrrole that have different ratios of stable crystal form to unstable crystal form may be blended, using blending methods known in the art, to achieve a desired ratio. The ratio of the polymorphs present in a particular batch of chlorfenapyr particles may be determined by infrared analysis.

The chlorfenapyr particles of the present invention preferably comprise a Polymorph I to Polymorph II ratio of about 1:3 to 1:0 and more preferably about 1:1 to 1:0.

The volume mean diameter of the arylpyrrole particles of this invention is preferably less than about 100 µm, more preferably less than about 15 µm, and most preferably about 0.5 µm to 10 µm.

The arylpyrrole particles of this invention may be formulated as suspension concentrates, dispersible granules, wettable powders, dusts, dust concentrates, microemulsions and the like, by methods well-known in the art. These compositions include the arylpyrrole particles of this invention and one or more agronomically acceptable solid or liquid carriers.

In particular, the present invention provides stable suspension concentrate compositions which comprise about 10% to 50% by weight of the arylpyrrole particles of this invention, about 0.1% to 2% by weight of a dispersing agent, about 0.5% to 5% by weight of a steric stabilizer, about 0.1% to 1% by weight of a suspending agent, about 0.01% to 0.5% by weight of a thickening agent, up to about 15% by weight of an antifreeze agent, up to about 1% by weight of an antifoam agent, up to about 0.5% by weight of a preservative, and water.

The stable suspension concentrate compositions of this invention preferably comprise 10% to 40% by weight of the arylpyrrole particles, 0.5% to 1.5% by weight of a dispersing agent, 1.5% to 3.5% by weight of a steric stabilizer, 0.1% to 1% by weight of a suspending agent, 0.01% to 0.5% by weight of a thickening agent, 5% to 10% by weight of an antifreeze agent, 0.1% to 1% by weight of an antifoam agent, 0.01% to 0.5% by weight of a preservative, and water.

In the suspension concentrate compositions of the present invention, the ratio of the total amount of the dispersing agent and the steric stabilizer to the arylpyrrole particles is preferably about 1:5 to 1:15 and more preferably about 1:8 to 1:10.

The volume mean diameter of the arylpyrrole particles present in the suspension concentrate compositions of this invention is preferably less than 15 µm, more preferably about 0.5 µm to 10 µm, and most preferably about 0.5 µm to 4 µm.

Arylpyrrole compounds of this invention include those having the structural formula I

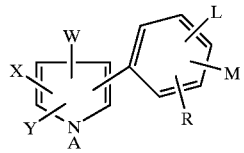

(I)

wherein
X is H, F, Cl, Br, I, $C_1$–$C_4$haloalkyl or $S(O)_m$($C_1$–$C_4$haloalkyl);
Y is F, Cl, Br, I, $C_1$–$C_4$haloalkyl or CN;
W is CN or $NO_2$;
A is $C_1$–$C_4$alkyl optionally substituted with
    one to three halogen atoms,
    one cyano,
    one hydroxy,
    one $C_1$–$C_4$alkoxy,
    one $C_1$–$C_4$alkylthio,
    one phenyl optionally substituted with
        $C_1$–$C_3$alkyl, $C_1$–$C_3$alkoxy, or
        one to three halogen atoms,
    one phenoxy optionally substituted with
        one to three halogen atoms, or
    one benzyloxy optionally substituted with
        one halogen atom,
$C_1$–$C_4$carbalkoxymethyl,
$C_3$–$C_4$alkenyl optionally substituted with one to three halogen atoms,
cyano,
$C_3$–$C_4$alkynyl optionally substituted with one halogen atom,
di-($C_1$–$C_4$alkyl)aminocarbonyl, or
benzoyl optionally substituted with one to three halogen atoms or one to three $C_1$–$C_4$alkyl groups;
L is H, F, Cl or Br;
M and R are each independently H, $C_1$–$C_3$alkyl, $C_1$–$C_3$alkoxy, $C_1$–$C_3$alkylthio, $C_1$–$C_3$alkylsulfinyl, $C_1$–$C_3$alkylsulfonyl, cyano, F, Cl, Br, I, nitro, $C_1$–$C_3$haloalkyl, $R_1CF_2Z$, $R_2CO$ or $NR_3R_4$, or when M and R are on adjacent positions and taken with the carbon atoms to which they are attached they may form a ring in which MR represents the structure:
    —$OCH_2O$—, —$OCF_2O$—, —$OCR_6R_7CR_8R_9O$—,
    —$OCH_2CH_2$—, —$OCH_2CH_2CH_2$— or —CH=CH—CH=CH—;
Z is $S(O)n$ or O;
$R_1$ is H, F, $CHF_2$, CHFCl or $CF_3$;
$R_2$ is $C_1$–$C_3$alkyl, $C_1$–$C_3$alkoxy or $NR_3R_4$;
$R_3$ is H or $C_1$–$C_3$alkyl;
$R_4$ is H, $C_1$–$C_3$alkyl or $R_5CO$;
$R_5$ is H or $C_1$–$C_3$alkyl;
$R_6$, $R_7$, $R_8$ and $R_9$ are each independently hydrogen, halogen or $C_1$–$C_3$alkyl; and
m and n are each independently an integer of 0, 1 or 2.

Preferred arylpyrrole compounds suitable for use in the present invention are those having the structural formula II

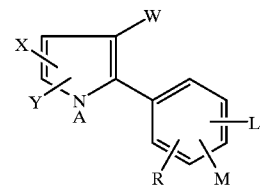

(II)

wherein X, Y, W, A, L, M and R are as described above.

More preferred arylpyrrole compounds which are particularly suitable for use in this invention are those having the structural formula II wherein
X and Y are each independently Cl, Br or $CF_3$;
W is CN;
A is $C_1$–$C_4$alkoxymethyl;
L is H or F;
M is H, F, Cl or Br; and
R is F, Cl, Br, $CF_3$ or $OCF_3$.

Another important aspect of this invention is a process for preparing stable arylpyrrole particles, which process comprises:
    a) providing a first mixture comprising arylpyrrole particles, a dispersing agent and water;
    b) holding the first mixture in a temperature range of about 25° C. to 80° C. to obtain an aged mixture; and c) milling the aged mixture, if necessary, to obtain stabilized arylpyrrole particles.

The process of the present invention is hereinafter sometimes referred to as the "stabilization process". In this context, stabilization refers to maintaining a relatively constant particle size. Stable particles do not grow significantly during storage at room temperature for up to three months or longer in a suspension concentrate composition.

It has now been discovered that when the stable polymorph content of the arylpyrrole is less than approximately 80%, especially less than about 50%, and most especially less than about 25% by weight, the stability of the arylpyrrole particles may be enhanced by the process of this invention. The amount of time needed to obtain a sufficiently aged mixture will vary, and will depend to some degree on the initial crystal form content, the particle size, and the temperature. The process of this invention is especially useful for stabilizing chlorfenapyr particles.

To overcome the problems associated with the use of arylpyrrole particles containing the less stable polymorph, it is desirable to subject all arylpyrrole particles to the stabilization process of this invention. The stabilization process of this invention is especially useful for improving the particle size stability of chlorfenapyr containing less than 80% of Polymorph I.

The volume mean diameter of the arylpyrrole particles utilized in the process of this invention is preferably less than about 100 $\mu$m and more preferably about 0.5 $\mu$m to 30 $\mu$m. The volume mean diameter of the stabilized arylpyrrole particles prepared by the stabilization process is preferably about 0.5 $\mu$m to 10 $\mu$m and more preferably about 0.5 $\mu$m to 4 $\mu$m.

Dispersing agents suitable for use in this invention include, but are not limited to, the salts of the condensation products of formaldehyde with the sulfonation products of polycyclic aromatic compounds; the salts of polyacrylic acids; the condensation products of fatty acids or aliphatic amines or amides containing at least about twelve carbon atoms in the molecule with ethylene oxide and/or propylene oxide; fatty acid esters of glycerol, sorbitan, sucrose or pentaerythritol and their condensation products with ethylene oxide and/or propylene oxide; condensation products of fatty alcohols or alkyl phenols with ethylene oxide and/or propylene oxide and their sulfates or sulfonates; and alkali or alkaline earth metal salts of sulfuric or sulfonic acid esters containing at least ten carbon atoms in the molecule, for example sodium lauryl sulfate and dodecylbenzene sulfonate.

Preferred dispersing agents include the salts of the condensation products of formaldehyde with the sulfonation products of polycyclic aromatic compounds such as the salts of the condensation products of formaldehyde with naphthalene sulfonates, petroleum sulfonates and lignin sulfonates. More preferred dispersing agents include the sodium sulfonate of naphthalene formaldehyde condensates such as MORWET® D425 (Witco, Houston, Tex.), LOMAR® PW (Henkel, Cincinnati, Ohio) and DARVAN® 1 (R.T. Vanderbilt Co., Norwalk, Conn.).

In a preferred process of the present invention, the first mixture is held in a temperature range of about 40° C. to 60° C. In another preferred process of this invention, the first mixture is preferably held in the temperature range for about 1 hour to 72 hours, more preferably for about 2 hours to 48 hours and most preferably for about 2 hours to 24 hours.

The first mixture of the present invention preferably comprises about 10% to 85% by weight of arylpyrrole particles, about 0.1% to 3.5% by weight of a dispersing agent, about 0.5% to 8.5% by weight of a steric stabilizer, about 0.1% to 2% by weight of a suspending agent, up to about 25% by weight of an antifreeze agent, up to about 2% by weight of an antifoam agent, up to about 1% by weight of a preservative, up to about 1% by weight of a thickening agent, and water.

More preferably, the first mixture comprises 20% to 70% by weight of arylpyrrole particles having a volume mean diameter of less than about 100 $\mu$m, 0.5% to 2.5% by weight of a dispersing agent, 1.5% to 6% by weight of a steric stabilizer, 0.1% to 2% by weight of a suspending agent, 5% to 20% by weight of an antifreeze agent, 0.1% to 2% by weight of an antifoam agent, 0.01% to 1% by weight of a preservative and water.

The present invention also provides suspension concentrate compositions which comprise about 10% to 50% by weight of stabilized arylpyrrole particles prepared by the process of this invention, about 0.1% to 2% by weight of a dispersing agent, about 0.5% to 5% by weight of a steric stabilizer, about 0.1% to 1% by weight of a suspending agent, about 0.01% to 0.5% by weight of a thickening agent, about 5% to 15% by weight of an antifreeze agent, up to about 1% by weight of an antifoam agent, up to about 0.5% by weight of a preservative, and water.

The suspension concentrate compositions of this invention preferably comprise 10% to 40% by weight of stabilized arylpyrrole particles having a volume mean diameter of 0.5 $\mu$m to 10 $\mu$m, 0.5% to 1.5% by weight of a dispersing agent, 1.5% to 3.5% by weight of a steric stabilizer, 0.1% to 1% by weight of a suspending agent, 0.01% to 0.5% by weight of a thickening agent, 5% to 10% by weight of an antifreeze agent, 0.1 % to 1% by weight of an antifoam agent, 0.01 % to 0.5% by weight of a preservative, and water.

In the suspension concentrate compositions and the preferred first mixtures of the present invention, the ratio of the total amount of the dispersing agent and the steric stabilizer to the appropriate arylpyrrole particles is preferably about 1:5 to 1:15 and more preferably about 1:8 to 15 1:10.

Steric stabilizers suitable for use in the present invention include, but are not limited to, polymers of ethylene oxide and copolymers of ethylene oxide and propylene oxide such as ethylene oxide/propylene oxide block copolymers. Preferred steric stabilizers are butyl-omega-hydroxypoly (oxypropylene)block polymers with poly(oxyethylene) having an average molecular weight in a range of about 2,400 to 3,500 with alpha-butyl-omega-hydroxy-ethylene oxide-propylene oxide block copolymers such as TOXIMUL® 8320 (Stepan Chemical Co., Winder, Ga.), WITCONOL® NS 500 LQ (Witco) and TERGITOL® XD (Union Carbide, Danbury, Conn.) being most preferred.

Suspending agents suitable for use in this invention include, but are not limited to, natural and synthetic clays and silicates, for example natural silicas such as diatomaceous earths; magnesium silicates such as talcs, magnesium aluminum silicates such as attapulgites and vermiculites; and aluminum silicates such as kaolinites, montmorillonites and micas. Preferred suspending agents are magnesium silicates, magnesium aluminum silicates and aluminum silicates with magnesium aluminum silicates such as VAN-GEL® ES (R.T. Vanderbilt), VEEGUM® (R.T. Vanderbilt), VEEGUM® T (R.T. Vanderbilt) and GELWHITE® (Southern Clay Products, Gonzales, Tex.) being most preferred.

Thickening agents useful in this invention include, but are not limited to, natural thickening agents such as xanthan gum, carrageenan, pectin, gum arabic, guar rubber and the like; semisynthetic thickening agents such as the methylation products, carboxyalkylation products and hydroxyalkylation products of cellulose or starch derivatives; and synthetic thickening agents such as polyacrylates, polymaleinates and polyvinylpyrrolidone with xanthan gums such as KELZAN® (Kelco, San Diego, Calif.) and RHODOPOL® 23 (Rhone-Poulenc, Cranbury, N.J.) being preferred thickening agents.

Antifreeze agents suitable for use in the present invention include glycols such as propylene glycol, ethylene glycol and the like with propylene glycol being preferred. Suitable antifoam agents include emulsions of silicone oils, emulsions of fatty alcohols and the like. Preservatives suitable for use in this invention include 1,2-benzisothiazolin-3-one, epichlorohydrin, phenylglycidyl ether, allylglycidyl ether, formaldehyde compositions and the like with 1,2-benzisothiazolin-3-one being preferred.

Suspension concentrate compositions of the present invention may conveniently be prepared by admixing arylpyrrole particles, a dispersing agent, a steric stabilizer, a suspending agent and an antifreeze agent with water to obtain a first mixture, holding the first mixture according to the process of this invention to obtain an aged mixture, milling the aged mixture to obtain a mixture comprising stabilized arylpyrrole particles, and admixing the mixture comprising stabilized arylpyrrole particles with a thickening agent and additional water to obtain the desired suspension concentrate composition The suspension concentrate compositions of this invention preferably have a pH of about pH 5 to pH 9 and more preferably about pH 6 to pH 8. To adjust the pH into the desired range, acids such as acetic acid, propionic acid, sulfuric acid, phosphoric acid, hydrochloric acid and the like may be used.

In order to facilitate a further understanding of the invention, the following examples are presented to illustrate more specific details thereof. The scope of the invention is not limited to the embodiments illustrated, but includes the entire subject matter of the appended claims.

EXAMPLE 1
Preparation of Stabilized Chlorfenapyr Particles

Propylene glycol (331 g), a 17% 1,2-benzisothiazolin-3-one solution (PROXEL® GXL, Zeneca) (6.35 g), a 30% silicone emulsion (AF 30 IND®, Harcros Chemical Co.) (29.9 g), an alpha-butyl-omega-hydroxyl-ethylene oxide/propylene oxide block copolymer (TOXIMUL® 8320, Stepan Chemical Co.)(132.5 g), a sodium sulfonate of a naphthalene formaldehyde condensate (MORWET® D425, Witco)(44 g), magnesium aluminum silicate (VANGEL® ES, R.T. Vanderbilt)(22.2 g), and chlorfenapyr (1,542 g, 90% real, 0% Polymorph I) are added sequentially with stirring to water (976 g). The resultant mixture is stirred until homogeneous and passed through a wet milling device to obtain a mixture identified as composition number 1 below comprising chlorfenapyr particles having a volume mean diameter of about 1.58 μm.

| Composition Number 1 | |
| --- | --- |
| Ingredient | wt/wt % |
| Chlorfenapyr | 50.00 |
| MORWET ® D425 | 1.43 |
| TOXIMUL ® 8320 | 4.30 |
| VANGEL ® ES | 0.72 |
| Propylene glycol | 10.73 |

-continued

| Composition Number 1 | |
| --- | --- |
| Ingredient | wt/wt % |
| AF 30 IND ® | 0.97 |
| PROXEL ® GXL | 0.21 |
| Water | 31.65 |

Individual samples of composition number 1 are stirred at 40° C., 55° C. and 70° C. for 17 hours and passed through a wet milling device to obtain composition numbers 2, 3 and 4 comprising stabilized chlorfenapyr particles. Composition numbers 1–4 are then stored at room temperature for two months and the volume mean diameter of the chlorfenapyr particles in each composition is measured. The results are summarized in Table I.

As can be seen from the data in Table I, the volume mean diameter of the stabilized chlorfenapyr particles present in composition numbers 2, 3 and 4 increases significantly less than the volume mean diameter of the chlorfenapyr particles present in composition number 1.

TABLE I

Stability of Chlorfenapyr Particles

| Comp. Number | Temperature (° C.) Stirred at for 17 Hours | Initial Volume Mean Diameter of Chlorfenapyr Particles (μm) | Volume Mean Diameter of Chlorfenapyr Particles (μm) After Storage at Room Temperature for 2 Months |
| --- | --- | --- | --- |
| 1 | N/A | 1.58 | 4.47 |
| 2 | 40 | 1.42 | 1.41 |
| 3 | 55 | 1.49 | 1.41 |
| 4 | 70 | 1.50 | 2.72 |

EXAMPLE 2

Effect of Initial Particle Size of Chlorfenapyr Particles

Using the same procedure as described in Example 1, but varying the particle size of the chlorfenapyr particles present in the compositions prior to holding at 55° C., composition numbers 5–7 comprising stabilized chlorfenapyr particles are obtained. Those compositions and composition number 8, which is identical to composition number 1 from Example 1 except that the chlorfenapyr particles have a volume mean diameter of 1.44 μm, are stored at room temperature for three weeks. The volume mean diameter of the chlorfenapyr particles in each composition is then measured and the results are summarized in Table II.

As can be seen from the data in Table II, the volume mean diameter of the stabilized chlorfenapyr particles present in composition numbers 5–7 increases significantly less than the volume mean diameter of the chlorfenapyr particles present in composition number 8.

It can also be seen that the smaller the particle size prior to the stabilizing process, the more effective the stabilizing process is.

TABLE II

Effect of Initial Particle Size of Chlorfenapyr Particles

| Composition Number | Volume Mean Diameter of Chlorfenapyr Particles ($\mu$m) Prior to Stabilization Process | Hours Stirred at 55° C. | Volume Mean Diameter of Stabilized Chlorfenapyr Particles ($\mu$m) | Weeks Stored at Room Temperature | Final Volume Mean Diameter of Chlorfenapyr Particles ($\mu$m) |
|---|---|---|---|---|---|
| 5 | >30 | 17 | 1.48 | 3 | 2.36 |
| 6 | 4.5 | 17 | 1.45 | 3 | 1.40 |
| 7 | 1.6 | 17 | 1.53 | 3 | 1.33 |
| 8* | 1.44 | — | — | 3 | 3.88 |

*not stabilized

EXAMPLE 3
Effect of Various Holding Periods

Using the same procedure as described in Example 1, but milling the chlorfenapyr particles present in the compositions to about 4 $\mu$m prior to holding at 55° C. for various periods of time, composition numbers 9–15 comprising stabilized chlorfenapyr particles are obtained. Composition numbers 9–15 and non-stabilized chlorfenapyr composition number 16, which is identical to composition number 1 in Example 1 except that the chlorfenapyr particles have a volume mean diameter of 1.41 $\mu$m, are stored at room temperature for three months. The volume mean diameter of the chlorfenapyr particles in each composition is then measured and the results are summarized in Table III.

As can be seen from the data in Table III, the volume mean diameter of the stabilized chlorfenapyr particles present in composition numbers 9–15 increases significantly less than the volume mean diameter of the chlorfenapyr particles present in composition number 16.

EXAMPLE 4
Effect of Various Chlorfenapyr Polymorph Ratios on Storage Stability of Chlorfenapyr Using the same procedure as described in Example 1, but using different batches of chlorfenapyr particles and holding at 55° C. for 17 hours, several compositions comprising stabilized chlorfenapyr particles are obtained and identified in Table IV. The compositions comprising the stabilized chlorfenapyr particles and the appropriate non-stabilized composition are stored at room temperature for various periods of time. The volume mean diameter of the chlorfenapyr particles in each composition is then measured and the results are summarized in Table IV.

As can be seen from the data in Table IV, chlorfenapyr particles present in stabilized compositions prepared using chlorfenapyr particles having less than about 80% Polymorph I are, in general, significantly more is stable than chlorfenapyr particles present in the corresponding non-stabilized compositions.

TABLE III

Effect of Various Holding Periods

| Composition Number | Volume Mean Diameter of Chlorfenapyr Particles ($\mu$m) Prior to Stabilization Process | Hours Stirred at 55° C. | Volume Mean Diameter of Stabilized Chlorfenapyr Particles ($\mu$m) | Final Volume Mean Diameter of Chlorfenapyr Particles ($\mu$m) After Storage at Room Temperature for 3 Months |
|---|---|---|---|---|
| 9 | 4.1 | 2 | 1.46 | 1.92 |
| 10 | 4.1 | 5 | 1.41 | 1.89 |
| 11 | 4.1 | 9 | 1.42 | 1.70 |
| 12 | 4.1 | 17 | 1.25 | 1.38 |
| 13 | 4.0 | 17 | 1.41 | 1.69 |
| 14 | 4.0 | 24 | 1.36 | 1.51 |
| 15 | 4.0 | 41 | 1.40 | 1.47 |
| 16* | 1.40 | — | — | 3.94 |

*not stabilized

TABLE IV

Effect of Various Polymorph Ratios

| Comp. Number | % Polymorph I | Volume Mean Diameter of Chlorfenapyr Particles (μm) Prior to Stabilization Process | Volume Mean Diameter of Stabilized Chlorfenapyr Particles (μm) | Weeks Stored at Room Temp. | Final Volume Mean Diameter of Chlorfenapyr Particles (μm) |
|---|---|---|---|---|---|
| 17 | 0 | 3.7 | 1.45 | 1 | 1.38 |
|    | 0 | 1.55 | not stabilized | 1 | 15.04 |
| 18 | 0 | 3.3 | 1.51 | 3 | 1.51 |
|    | 0 | 1.45 | not stabilized | 3 | 1.56 |
| 19 | 14 | 4.4 | 1.39 | 8 days | 1.88 |
|    | 14 | 1.36 | not stabilized | 1 | 2.41 |
| 20 | 14 | 1.9 | 1.53 | 12 | 1.48 |
|    | 14 | 1.45 | not stabilized | 12 | 2.10 |
| 21 | 20 | 2.8 | 1.76 | 6 | 1.97 |
|    | 20 | 1.32 | not stabilized | 6 | 5.05 |
| 22 | 20 | 3.1 | 1.76 | 6 | 1.64 |
|    | 20 | 1.63 | not stabilized | 6 | 2.55 |
| 23 | 20 | 4.0 | 1.37 | 2 | 1.28 |
|    | 20 | 1.18 | not stabilized | 2 | 1.25 |
| 24 | 23 | 3.5 | 1.37 | 9 days | 2.75 |
|    | 23 | 1.55 | not stabilized | 11 days | 5.82 |
| 25 | 55 | 3.4 | 1.56 | 12 | 1.75 |
|    | 55 | 1.47 | not stabilized | 12 | 1.84 |
| 26 | 56 | 4.5 | 1.48 | 12 | 1.48 |
|    | 56 | 1.55 | not stabilized | 12 | 1.59 |
| 27 | 65 | 3.2 | 1.45 | 16 | 1.55 |
|    | 65 | 1.42 | not stabilized | 16 | 1.54 |
| 28 | 76 | 2.9 | 1.38 | 3 | 1.45 |
|    | 76 | 1.01 | not stabilized | 3 | 1.36 |
| 29 | 80 | 3.4 | 1.66 | 6 | 1.62 |
|    | 80 | 1.45 | not stabilized | 6 | 1.39 |
| 30 | 87 | 2.9 | 1.56 | 12 | 1.63 |
|    | 87 | 1.71 | not stabilized | 12 | 1.71 |

EXAMPLE 5

Effect of Various Polymorph Ratios on Storage Stability of Chlorfenapyr Suspension Concentrate Compositions Propylene glycol (730 g), a 17% 1,2-benzisothiazolin-3-one solution (PROXEL® GXL, Zeneca)(14.0 g), a 30% silicone emulsion (AF 30 IND®, Harcros Chemical Co.) (66.0 g), alpha-butyl-omega-hydroxyl-ethylene oxide/propylene oxide block copolymer (TOXIMUL® 8320, Stepan Chemical Co.)(292 g), sodium sulfonate of naphthalene formaldehyde condensate (MORWET®) D425, Witco) (97.0 g), magnesium aluminum silicate (VANGEL® ES, R.T. Vanderbilt)(49.0 g) and chlorfenapyr (3,400 g, 90% real, 6.7:1 Polymorph I to Polymorph II ratio) are added sequentially with stirring to water (2,152 g). The resultant mixture is stirred until homogeneous and passed through a wet milling device to obtain a mill base wherein the chlorfenapyr particles have a volume mean diameter of about 1.5 μm. The mill base is charged into a vessel, agitated and adjusted to a pH of pH 6.5 to pH 7.2 with acetic acid (19.0 g). A 1% xanthan gum gel (1,459 g)(previously prepared from xanthan gum (15.0 g), a 17% 1,2-benzisothiazolin-3-one solution (PROXEL® GXL, Zeneca)(1.0 g) and water (1,443 g)) and water (1,453 g) are added to the pH adjusted mill base and mixing is continued to obtain the suspension concentrate composition identified below as composition number 31.

| Composition Number 31 | |
|---|---|
| Ingredient | wt/wt % |
| Chlorfenapyr[1] | 34.94 |
| MORWET ® D425 | 1.00 |
| TOXIMUL ® 8320 | 3.00 |
| VANGEL ® ES | 0.50 |
| Propylene Glycol | 7.50 |
| AF 30 IND ® | 0.68 |
| PROXEL ® GXL | 0.15 |
| Xanthan Gum | 0.15 |
| Acetic Acid | 0.20 |
| Water | 51.88 |

[1]Polymorph I to Polymorph II ratio is 6.7:1

Using the same procedure, but varying the Polymorph I to Polymorph II ratio, the suspension concentrate compositions identified as composition numbers 32–38 in Table V are obtained. Samples of the suspension concen- trate compositions are stored at room temperature for various periods of time. The volume mean diameter of the chlorfenapyr particles in each sample is then measured and the results are summarized in Table V.

As can be seen from the data in Table V, chlorfenapyr particles comprising a Polymorph I to Polymorph II ratio of greater than about 1:4 (composition numbers 31–35) are significantly more stable than chlorfenapyr particles comprising a Polymorph I to Polymorph II ratio of 1:4 to 0:1 (composition numbers 36–38).

TABLE V

Effect of Various Polymorph Ratios

| Composition Number | Ratio of Polymorph I to Polymorph II | Initial Volume Mean Diameter of Chlorfenapyr Particles ($\mu$m) | Weeks Stored at Room Temperature | Final Volume Mean Diameter of Chlorfenapyr Particles ($\mu$m) | % Increase/ (Decrease) in Volume Mean Diameter of Chlorfenapyr Particles |
|---|---|---|---|---|---|
| 31 | 6.7:1 | 1.55 | 4 | 1.38 | (12) |
|    |       |      | 8 | 1.40 | (11) |
| 32 | 2:1   | 1.59 | 8 | 1.40 | (14) |
| 33 | 1:1   | 1.96 | 3 | 2.26 | 15 |
|    |       |      | 8 | 2.03 | 4 |
| 34 | 1:1.3 | 1.55 | 8 | 1.59 | 3 |
| 35 | 1:3   | 2.3  | 3 | 2.77 | 20 |
|    |       |      | 8 | 2.41 | 5 |
| 36 | 1:4   | 1.32 | 6 | 5.05 | 283 |
| 37 | 1:6.1 | 1.58 | 4 | 2.49 | 58 |
|    |       |      | 8 | 2.57 | 63 |
|    |       |      | 12 | 2.60 | 65 |
| 38 | 0:1   | 1.56 | 1 | 7.93 | 408 |
|    |       |      | 4 | 7.06 | 353 |
|    |       |      | 8 | 7.17 | 360 |

What is claimed is:

1. A stable arylpyrrole particle comprising an arylpyrrole which can exist as one or two different polymorphs, at least one of which is particle size stable during storage, wherein the ratio of stable polymorph to unstable polymorph in said particle is greater than about 1:4, said arylpyrrole being represented by the formula

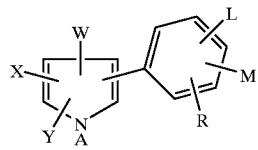

wherein
X is H, F, Cl, Br, I, $C_1$–$C_4$haloalkyl or $S(O)_m$($C_1$–$C_4$haloalkyl);
Y is F, Cl, Br, I, $C_1$–$C_4$haloalkyl or CN;
W is CN or $NO_2$;
A is $C_1$–$C_4$alkyl optionally substituted with
  one to three halogen atoms,
  one cyano,
  one hydroxy,
  one $C_1$–$C_4$alkoxy,
  one $C_1$–$C_4$alkylthio,
  one phenyl optionally substituted with
    $C_1$–$C_3$alkyl, $C_1$–$C_3$alkoxy, or
    one to three halogen atoms,
  one phenoxy optionally substituted with
    one to three halogen atoms, or
  one benzyloxy optionally substituted with
    one halogen atom,
  $C_1$–$C_4$carbalkoxymethyl,
  $C_3$–$C_4$alkenyl optionally substituted with one to three halogen atoms,
  cyano,
  $C_3$–$C_4$alkynyl optionally substituted with one halogen atom,
  di-($C_1$–$C_4$alkyl)aminocarbonyl, or
  benzoyl optionally substituted with one to three halogen atoms or one to three $C_1$–$C_4$alkyl groups;
L is H, F, Cl or Br;
M and R are each independently H, $C_1$–$C_3$alkyl, $C_1$–$C_3$alkoxy, $C_1$–$C_3$alkylthio, $C_1$–$C_3$alkylsulfinyl, $C_1$–$C_3$alkylsulfonyl, cyano, F, Cl, Br, I, nitro, $C_1$–$C_3$haloalkyl, $R_1CF_2Z$, $R_2CO$ or $NR_3R_4$, or when M and R are on adjacent positions and taken with the carbon atoms to which they are attached they may form a ring in which MR represents the structure:
  —$OCH_2O$—, —$OCF_2O$—, —$OCR_6R_7CR_8R_9O$—,
  —$OCH_2CH_2$—, —$OCH_2CH_2CH_2$— or —CH=CH—CH=CH—;
Z is $S(O)n$ or O;
$R_1$ is H, F, $CHF_2$, CHFCl or $CF_3$;
$R_2$ is $C_1$–$C_3$alkyl, $C_1$–$C_3$alkoxy or $NR_3R_4$;
$R_3$ is H or $C_1$–$C_3$alkyl;
$R_4$ is H, $C_1$–$C_3$alkyl or $R_5CO$;
$R_5$ is H or $C_1$–$C_3$alkyl;
$R_6$, $R_7$, $R_8$ and $R_9$ are each independently hydrogen, halogen or $C_1$–$C_3$alkyl; and
m and n are each independently an integer of 0, 1 or 2.

2. A particle according to claim 1 wherein said arylpyrrole is represented by the formula

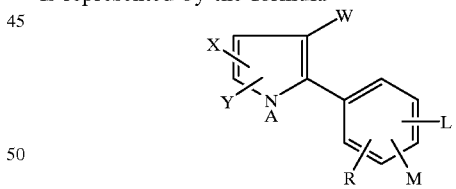

wherein X, Y, W, A, L, M and R are as defined in claim 1.

3. A particle according to claim 2 wherein
X and Y are each independently Cl, Br or $CF_3$;
W is CN;
A is $C_1$–$C_4$alkoxymethyl;
L is H or F;
M is H, F, Cl or Br; and
R is F, Cl, Br, $CF_3$ or $OCF_3$.

4. A particle according to claim 3 wherein said arylpyrrole is chlorfenapyr.

5. A particle according to claim 4 wherein said ratio is about 1:1 to 1:0.

* * * * *